United States Patent [19]

Sonnewald et al.

[11] Patent Number: 5,492,820
[45] Date of Patent: Feb. 20, 1996

[54] PLASMIDS FOR THE PRODUCTION OF TRANSGENIC PLANTS THAT ARE MODIFIED IN HABIT AND YIELD

[75] Inventors: Uwe Sonnewald; Lothar Willmitzer, both of Berlin, Germany

[73] Assignee: Institut Fur Genbiologische Forschung Berlin GmbH, Germany

[21] Appl. No.: 147,007

[22] Filed: Nov. 2, 1993

Related U.S. Application Data

[63] Continuation of Ser. No. 788,921, Nov. 7, 1991, abandoned.

[30] Foreign Application Priority Data

Nov. 8, 1990 [DE] Germany ............... 40 35 756.2

[51] Int. Cl.$^6$ ............... C12N 15/00; C12N 15/82; C12N 15/31; C12N 15/55
[52] U.S. Cl. ............... 435/172.3; 435/320.1; 435/69.1; 435/195; 435/100; 435/105; 800/205; 800/DIG. 40; 800/DIG. 42; 800/DIG. 43
[58] Field of Search ............... 800/205; 435/172.3, 435/69.1, 240.4, 195, 320.1, 100, 105

[56] References Cited

U.S. PATENT DOCUMENTS 4,771,002  9/1988  Gelvin ............... 435/172.3

FOREIGN PATENT DOCUMENTS

| | | |
|---|---|---|
| 438904 | 7/1991 | European Pat. Off. . |
| 442592 | 8/1991 | European Pat. Off. . |
| 479359 | 4/1992 | European Pat. Off. . |
| 012386 | 12/1989 | WIPO . |
| 012876 | 11/1990 | WIPO . |

OTHER PUBLICATIONS von Schaewen, A., et al. EMBO Journal, vol. 9 (1990) pp. 3033–3040.
Metzler, D. E., *Biochemistry*, N.Y., N.Y., Academic Press, Inc., 1977, pp. 381, 635–636, 659–660.
Xu, D.-P., et al. Plant Physiology, vol. 90 (1989), pp. 635–642.
Cseke, C., et al. Trends in Biochemical Sciences, vol. of Dec. 1984, pp. 533–535.
Gallie, D. R., et al. Nucleic Acids Research, vol. 15 (1987) pp. 3257–3273.
Eckes, P., et al. Molecular & General Genetics (1986) vol. 205, pp. 14–22.
R. Horsch et al. Science, vol. 227 (1985) pp. 1229–1231.
M. Khalafalla et al. Hort Science, vol. 25 (1) (1990) pp. 103–105.
J. Togretti et al. Physiologia Plantarium, vol. 78 (1990) pp. 554–559.
G. Promachandra J. Plant Physiol., vol. 135 (3) (1989) pp. 257–260.
R. Lahti et al. J. Bacteriology, vol. 170, #12 (Dec. '88) pp. 5901–5907.
D. Metzler, Biochemistry, The Chemical Reactions of Living Cells, NY, Academic Press, 1977, pp. 635–636, 658, 659, 687–688.
S. Sheerman et al. Plant Cell Reports, vol. 7 (1988) pp. 13–16.
M. Keil et al. EMBO J., vol. 8, No. 5 (1989) pp. 1323–1330.
K. Lindsey et al. J. Exp. Botany, vol. 41, #226 (1990) pp. 529–536.
V. Sarafian et al. Plant Physiol., vol. 91 (1989) pp. 34–38.
K. McCue et al. TIBTECH, vol. 8 (Dec. '90) pp. 358–362.
T. Jellito et al. Planta, vol. 188 (1992) pp. 238–244.
J. Salinas et al. Nucleic Acids Res., vol. 16 (1988) pp. 4269–4285.
A. Fersht, "Enzyme Structure & Mechanism", W. H. Freeman & Co., Ltd., Reading, 1977, pp. 134–149.
"Evolutionary Conservation of the Active Site of Soluble Inorganic Pyrophosphatase," Barry S. Cooperman, et al.; Elsevier Science Publishers (1992), pp. 262–266.
"Primary Structure of the Inorganic Pyrophosphatase from Terhmophilic Bacterium PS–3," Tetsuroh Ichiba, et al.; J. Biochem (1990), pp. 572–578.
"Cloning and Characterization of an Inorganic Pyrophosphatase Gene from Arabidopsis Thaliana," Joseph J. Kieber, et al.; Plant Molecular Biology (1991), pp. 345–348.
"Nucelotide Sequence of S. Pombe Inorganic Pyrophosphatase," I. Kawasaki, et al.; Nucleic Acids Research, vol. 18, No. 19 (1990), p. 5888.
"Molecular Cloning and Functional Expression of cDNA Encoding a Mammalian Inorganic Pyrophosphatase," Zhaohuai Yang, et al.; The Journal of Biological Chemistry (1992), pp. 24641–24647.
"Yeast PPA2 Gene Encodes a Mitochondrial Inorganic Pyrophosphatase that is Essential for Mitochondrial Function," Maria Lundin, et al.; The Journal of Biological Chemistry (1991), pp. 12168–12172.
"Cloning, Molecular Characterization and Chromosome Localization of the Inorganic Pyrophosphatase (PPA) Gene from *S. cerevisia*," Lee F. Kolakowski Jr., et al.; Nucleic Acids Research, vol. 16, No. 22 (1988); pp. 10441–10453.
*J. Bacteriol* vol. 170, No. 12, 1988, pp. 5901–5907; Lahti R., et al., Cloning and Characterization of the Gene Encoding Inorganic Pyrophosphatase of *Escherichia–coli* K–12.'*Embo Journal*, vol. 9, No. 10, Oct. 1990, Eynsham, Oxford GB von Schaewen, A., et al., "Expression of a Yeast–Derived Invertase in the Cell Wall of Tobacco and Arabidopsis Plants Leads to Accumulation of Carbohydrate and Inhibition of Photosynthesis and Strongly Influences Growth and Phenotype of Transgenic Tobacco Plants".
Biological Abstracts BR39:88750 *abstract* & Plant Physiol. 7th Congress of the Federation of European Societies of Plant Physiology, UMEA Sweden, Aug. 5–10, 1990. Mooney P., et al., "Alteration in Glycolytic Intermediates by Genetic Manipulation of Phosphofructokinase".

*Primary Examiner*—David T. Fox
*Assistant Examiner*—Charles C. P. Rories
*Attorney, Agent, or Firm*—Ostrolenk, Faber, Gerb & Soffen

[57] ABSTRACT

Plasmids that comprise a DNA sequence coding for a protein that modifies the metabolism of soluble sugars, for example, an inorganic pyrophosphatase agent and plant cells comprising those plasmids, for the production of transgenic plants that are modified in habit and yield arc described, the plants being modified in habit by the transfer and the expression of genes that intervene in sugar metabolism or sugar distribution inside a plant.

13 Claims, 6 Drawing Sheets

Glucose mmol / m2

Fig. 4 B

Fructose mmol / m2

Fig. 4 C

Sucrose mmol / m2

Fig. 4 D

Starch mmol / m2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 73 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:1:

```
GGTACCTTTA  CAACAATTAC  CAACAACAAC  AAACAACAAA  CAACATTACA  ATTACTATTT    60

ACAATTACCA  TGG                                                           73
```

( 2 ) INFORMATION FOR SEQ ID NO:2:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:2:

```
TTTACAACAA  TTACCAACAA  CAACAAACAA  CAAACAACAT  TACAATTACT  ATTTACAATT        60
A                                                                              61
```

PLASMIDS FOR THE PRODUCTION OF TRANSGENIC PLANTS THAT ARE MODIFIED IN HABIT AND YIELD

This is a Continuation of application Ser. No. 07/788,921 filed on Nov. 7, 1991 now abandoned.

BACKGROUND OF THE INVENTION

The present invention relates to plasmids for the production of transgenic plants that are modified in habit and yield.

The growth, development and yield of a productive plant or an ornamental plant depend on the energy that the plant obtains by fixing $CO_2$ in carbohydrates during photosynthesis. The primary locations for photosynthesis are the leaf and, to a lesser extent, the stem tissue, whereas other plant organs, such as roots, seeds or tubers, make no substantial contribution to the formation of photoassimilates but, on the contrary, are dependent as regards their growth on being supplied by photo-synthetically active organs. That means that there is a flow of photosynthetically obtained energy from photosynthetically active tissues to photosynthetically inactive parts of a plant.

The photosynthetically active tissues are referred to as sources. They are defined as net exporters of fixed carbon dioxide. The photosynthetically inactive parts of a plant are referred to as "sinks". They are defined as net importers of photosynthetically fixed carbon dioxide.

It is to be assumed that both the efficient use of products of photosynthesis and their distribution within a plant have a strong influence on the plant in several respects. The habit of plants may be mentioned as an example. Newly developing organs such as very young leaves, or other regions such as the root and seeds, are completely dependent on the photosynthetic capacity of the sources. That means that the development of such organs is dependent on the distribution inside the plant of the photoassimilates formed in the sources. The possibility of forming young leaves, or of forming roots, could have drastic effects on the habit of a plant, such as, for example, the size of a plant, the internodal distance, the size and shape of a leaf, the appearance of a leaf and the amount and shape of the root formed. Furthermore, the distribution of photoassimilates is assumed to be of very crucial importance for the yield of a plant. Thus, the total photosynthetic capacity of wheat has not changed substantially in the last few decades, whereas the harvestable yield of wheat plants for humans has increased. This is largely attributable to the fact that the ratio between competing sinks has been changed to the effect that the sinks that are important for the yield, such as seeds, take up considerably more photoassimilate than do other regions of the plant that are not important for the yield, such as, for example, the stalk. It was thus possible by, in this case, shortening the haulm to obtain in wheat a sink to source ratio that is much more favourable for humans. That underlines the importance in higher plants, in relation to both the habit and the yield of plants, of the distribution of photoassimilates formed in the primary sources.

Modifications in habit, resistance to dryness and/or frost and especially modification in the yield of plants are considerable improvements over known plants.

Biotechnological processes for the genetic modification of dicotyledonous and monocotyledonous plants are known (Gasser and Fraley, 1989, Science 244, 1293–1299).

It is not known what biochemical mechanisms regulate the ratio of sink to source.

SUMMARY OF THE INVENTION

An object of the present invention is to provide plants that are modified in their habit, such as size, leaf shape, internodal distance, cell wall structure, seed, bulb and root formation, and especially in their yield on harvesting.

The present invention provides a plant which comprises a DNA coding for a protein that modifies sugar metabolism or sugar distribution. The DNA sequence is expressed in the resulting transgenic plant, which leads, for example, to an increase, in those transgenic plants, in the proportion of photoassimilates that are present in the form of soluble sugars in the source leaves.

For the purpose, plasmids are provided that comprise a DNA sequence: coding for a protein that modifies the metabolism of soluble sugars, those plasmids being inserted into plant cells and those cells being regenerated to whole plants. The product coded for by the DNA sequence preferably intervenes in the phosphate/pyrophosphate metabolism, the DNA sequence being especially a DNA sequence of an inorganic pyrophosphatase gene.

In most plants, photoassimilates are distributed within a plant in the form of sugars, and preferentially in the form of sucrose. Because sucrose is the most important form of transport for carbohydrates from source to sinks, another important determinant for the strength of a source, and therefore the efficient supply to sinks, could be the availability and content of soluble sugars (various mono-, di- and tri-saccharides, such as, for example, fructose, glucose and sucrose) in the leaves. For example, a relatively high content of sucrose in the source leaves should result in an increased supply to sinks and, accordingly, also in an increased proportion of photoassimilates in the harvestable organs. That would lead to an increase in yield.

The ratio between soluble sugars and starch in the source leaves is assumed to be of decisive importance for the distribution of carbohydrates between sink and source parts of a plant. An efficient supply of sinks with sucrose from the source leaves should lead to a modification in the habit of the plant, but especially to an increase in yield, which is in most cases determined by the sink store, such as seed and tuber or root.

One of the important control points in sucrose biosynthesis is the conversion of fructose-1,6-diphosphate (Fru-1,6-P2) into fructose-6-phosphate (Fru-6-P). One of the enzymes involved in that step is the pyrophosphate: fructose-6-phosphate-1-phosphotransferase (PFP). That enzyme can on the one hand convert Fru-1,6-P2 into Fru-6-P, with the release of inorganic pyrophosphate, and can on the other hand phosphorylate Fru-6-P into Fru- 1,6-P2, with the consumption of inorganic pyrophosphate. The direction of the reaction, which is catalysed by PFP, is controlled by the relative content of inorganic pyrophosphate and inorganic phosphate.

Continuous removal of inorganic pyrophosphate by an inorganic pyrophosphatase should bring about a shift in the above equilibrium in the direction of Fru-6-P and accordingly an increased formation of soluble sugars, such as, for example, hexoses and/or sucrose. A shift in the distribution of the photoassimilates by removing the pyrophosphate using an inorganic pyrophosphatase should also cause the reaction, catalysed by UDP-glucose-pyrophosphorylase, glucose-1-phosphate+UTP→UDP-glucose+PPi to be shifted in the direction of UDP glucose. The thus increased provision of UDP glucose leads to other modified properties of the plant, such as, for example, thicker cell walls. That is effected by increased provision of the precursors for cell wall biosynthesis. The thickening of the cell walls leads to an increase in the resistance to dryness in those plants, which is brought about by a reduced rate of transpiration.

A large number of cloning vectors comprising a replication system in *E. coli* and a marker that permits selection of the transformed cells are available for preparation for the insertion of foreign genes into higher plants. The vectors comprise, for example, pBR 322, pUC series, M13 mp series, pACYC 184, etc. Accordingly, the sequence can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoreses and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, have to be used as the flanking regions of the genes to be inserted.

The use of T-DNA for the transformation of plant cells has been intensively researched and sufficiently described in EP 120 516; Hoekema, In: The Binary Plant Vector System Offset-drukkerij Kanters B. V., Alblasserdam, 1985, Chapter V; Fraley et al., Crit. Rev. Plant Sci., 4: 1–46 and An et al., EMBO J. (1985) 4: 277–287.

Once the inserted DNA has been integrated in the genome it is relatively stable there and, as a rule, does not come out again. It normally contains a selection marker that confers on the transformed plant cells resistance to a biocide or an antibiotic, such as kanamycin, G 418, bleomycin, hygromycin or chloramphenicol, inter alia. The individually employed marker should accordingly permit the selection of transformed cells rather than cells that do not contain the inserted DNA.

It has now been found that a plasmid that comprises a DNA sequence that can be fused to the regulatory region of one or more other genes capable of bringing about expression of the gene in a plant cell or in a plant. The regulatory region comprises the promotor region of a plant gene and the termination signal of the same or of a different plant gene.

It is possible to use a promotor, for example, the cauliflower mosaic virus promotor (CaMV) that brings about constitutive expression and a plant termination signal. Other possible promtors are promotors encoding an expression specifically only in photosynthetically active cells (e.g. the ST-Ls1 promotor, Stockhaus et al., EMBO J. 8, 2445–2451) which should be a special advantage when a change in the sucrose metabolism is to be reached in leaves; a source-specific promotor active only during loading of sink-organs (i.e. at a special developmental phase;) a root-specific promotor, if a specific expression in roots is advantageous due to e.g. a thicker cell wall which is necessary; a storage-sink-specific promotor (being active e.g. only in tubers of potato, tap root of sugar beet, fruits of tomato like is the case for the class I patatin promotor) if the changes to be achieved are specifically advantageous for a sink tissue.

A plant termination signal may comprise the 3'-end of the poly-A side of the octopine synthase gene.

A large number of techniques are available for inserting DNA into a plant host cell. Those techniques include transformation with T-DNA using *Agrobacterium tumefaciens* or *Agrobacterium rhizogenes* as transformation agent, fusion, injection or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al., Mol. Gen. Genet. (1978), 163: 181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. The plants can be grown in the normal manner and crossed with plants that have the same transformed hereditary factors or other hereditary factors. The resulting hybrid individuals have the corresponding phenotypic properties.

Terms and Abbreviations

Abbreviations bp, kb=base pairs, kilobases

DNA=deoxyribonucleic acid, carrier of genetic information
HEPES=N-2-hydroxyethylpiperazine-N'-2-ethanesulphonic acid
SDS=sodium dodecyl sulphate
tris=tris(2-aminoethyl)amine
EDTA=ethylenediaminetetraacetic acid
U=unit (enzyme unit)

The following plasmids were deposited at the Deutsche Sammlung von Mikroorganismen (DSM) in Braunschweig, Federal Republic of Germany on 20 Aug. 1990 and on 10 Oct. 1991 (deposit number):

plasmid p35S-Ω-ppase (DSM 6141)—20 Aug. 1990
plasmid L-700:ppa (DSM 6733)—10 Oct. 1991

DETAILED DESCRIPTION OF THE FIGURES

Figure 1:
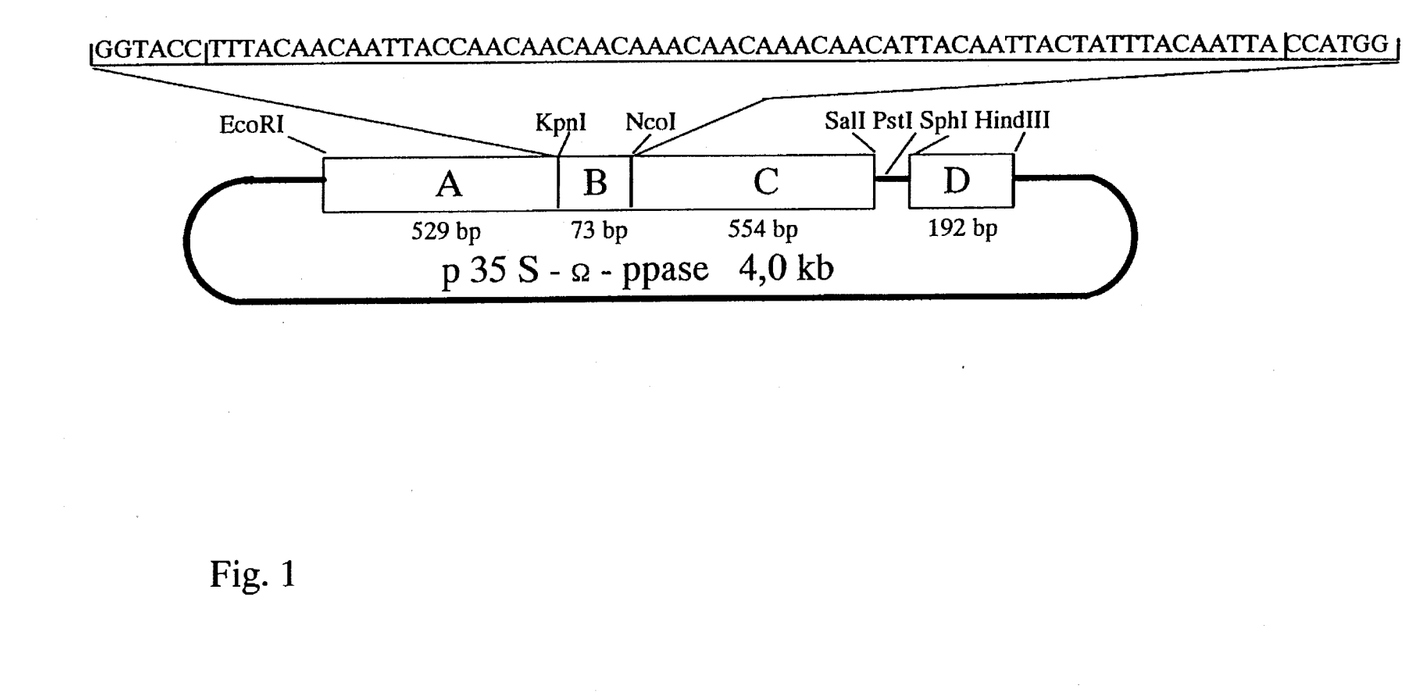
FIG. 1 shows the structure of the 4.0 kb plasmid p35S-Ω-ppase.

FIG. 1 shows the structure of the 4.0 kb plasmid p35S-Ω-ppase. The plasmid comprises the following fragments:

A=Fragment A (529 bp): contains the 35S promoter of cauliflower mosaic virus (CaMV). That fragment includes the nucleotides 6909 to 7437 of CaMV.

B=Fragment B (73 bp) SEQ ID NO:1: contains 61 nucleotides SEQ ID NO:2 of sequence:
TTTACAACAATTACCAACAACAACAAA-CAACAAACAACATTACAATTACTATTTA-CAATTA
the Asp 718 linker of sequence GGTACC is located at the 5'-end of the above sequence and the NcoI linker of sequence CCATGG is locataed at the 3'-end.

C=Fragment C (554 bp): contains the protein-coding region of the inorganic pyrophosphatase (ppa) from *E. coli* (nucleotides positions +39 to +565 of the sequence according to Lahti et al.).

D=Fragment D (192 bp): contains the polyadenylation signal of gene 3 of the T-DNA of the Ti-plasmid pTiACH5.

The cleavage sites described in the Example are also shown.

Figure 2:
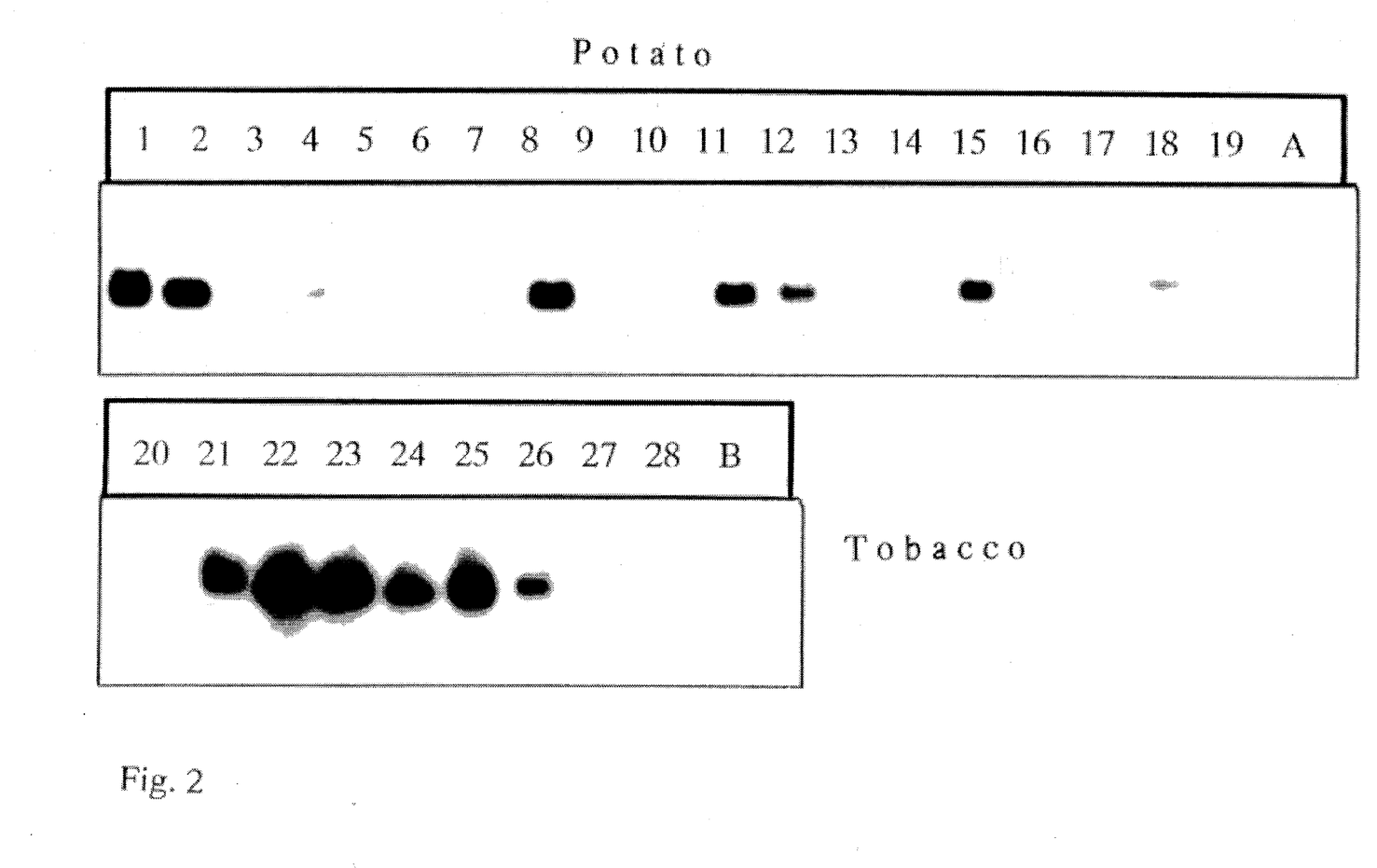
FIG. 2 shows detection of pyrophosphatase RNA in transgenic potato and tobacco plants, after Northern blot analysis.

FIG. 2 shows the detection of the RNA, coded for by the pyrophosphatase gene, in transgenic potato and tobacco plants by means of Northern blot analysis.

Positions 1 to 19: Samples of the total RNA obtained from leaves of potato plants that have been transformed with plasmid p35S-Ω-ppase and regenerated Positions 20 to 28: Samples of the total RNA obtained from leaves of tobacco plants that have been transformed by the plasmid p35S-Ω-ppase and regenerated Position A: Sample from an untransformed potato plant
Position B: Sample from an untransformed tobacco plant
The black spots indicate the RNA coded for by the pyrophosphatase.

Figure 3:
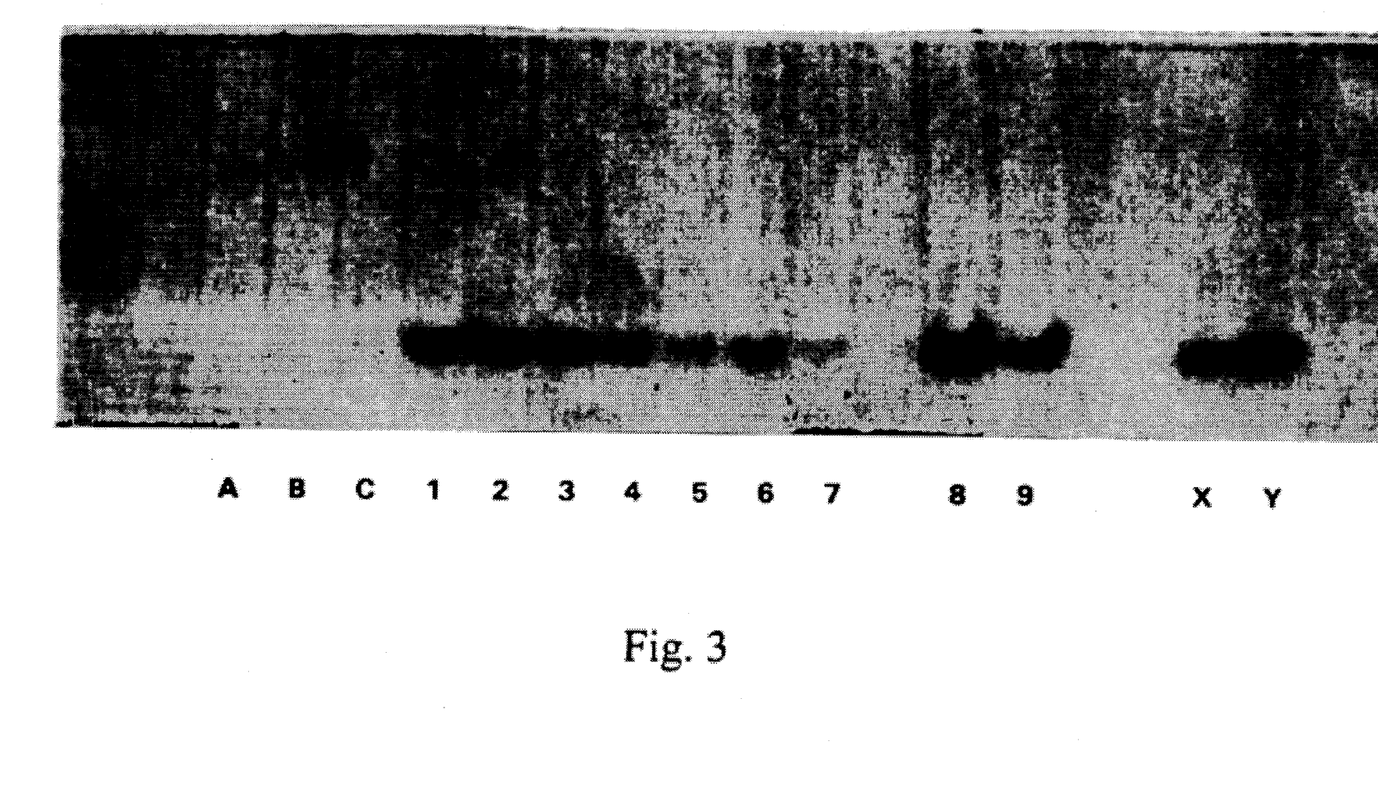
FIG. 3 shows detection of pyrophosphatase activity in protein extracts from leaves of transgenic potato and tobacco plants, after SDS polyacrylamide gel electrophoresis.
Figure 4A:
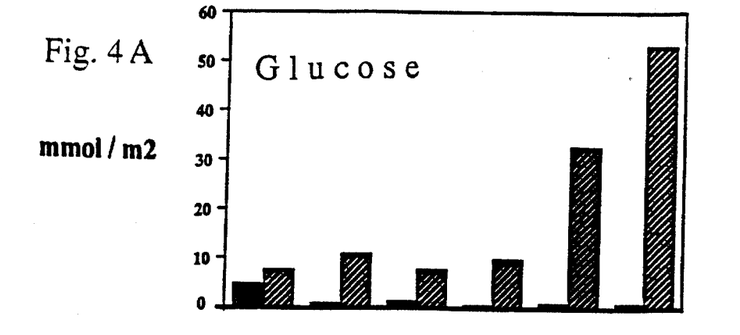
FIGS. 4A, 4B, 4C, and 4D show starch and soluble sugar content in leaves of different age from an untransformed tobacco plant, and in leaves of a tobacco plant transformed with the p35S-Ω-ppase plasmid.
Figure 4B:
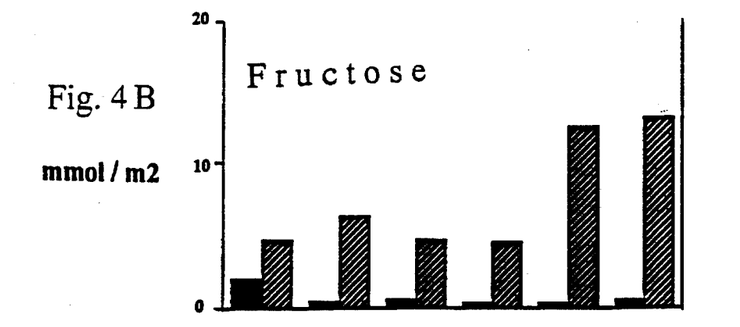
Figure 4C:
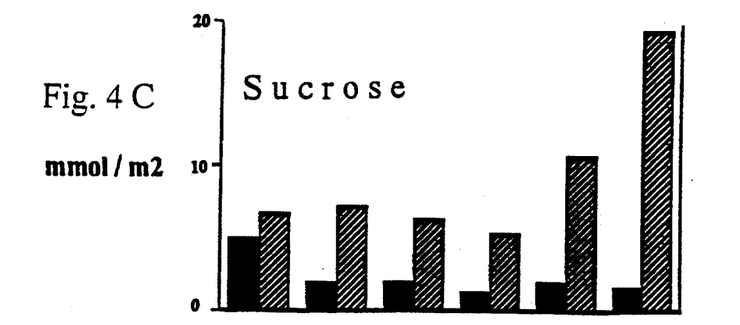
Figure 4D:
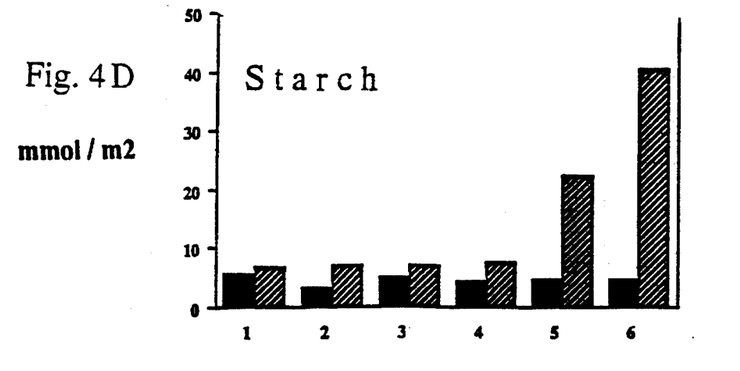

FIG. 3 shows the detection of the occurrence of new pyrophosphatase activity in protein extracts from leaves of the transgenic potato and tobacco plants transformed by the p35S-Ω-ppase plasmid, in a SDS polyacrylamide gel.

Positions 1 to 7: Protein extract from leaves of transformed potato plants
Positions 8 and 9: Protein extract from leaves of transformed tobacco plants
Position A: Protein extract from leaves of untransformed tobacco plants
Positions B and C: Protein extract from leaves of untransformed potato plants
Positions X and Y: Protein extract from *E. coli*

FIGS. 4A, 4B, 4C, and 4D show a comparison between the content of glucose, fructose, sucrose and starch in mmol/m$^2$ in a tobacco plant (▨) that expresses the 35S-Ω-ppase gene and in an untransformed tobacco plant (■) in leaves of different age.

In the FIG.:
1=very young leaves
2–4=mature leaves
5–6=old leaves

Figure 5:
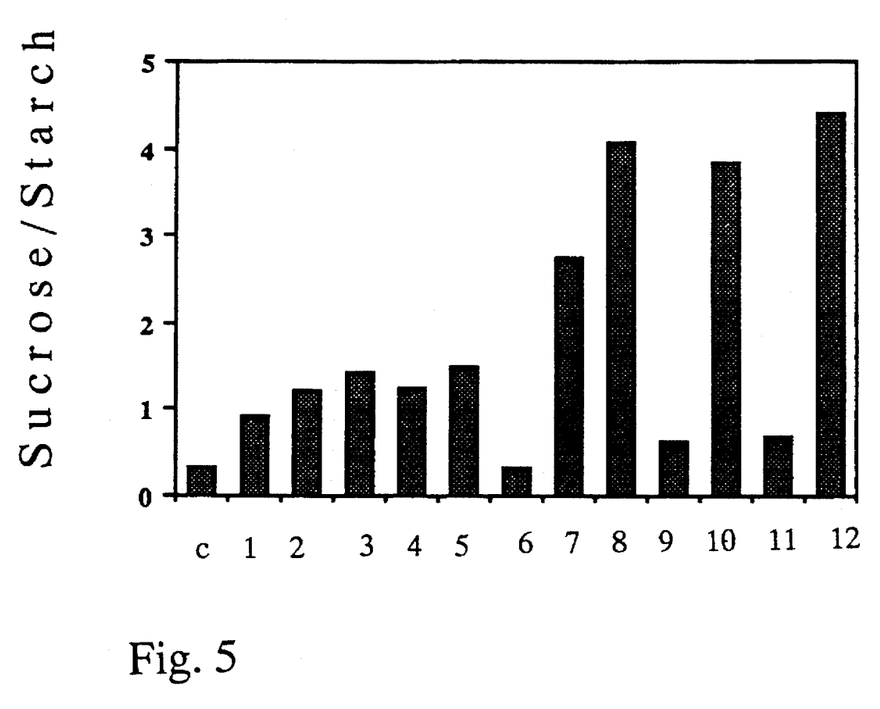
FIG. 5 shows the sucrose/starch ratio in leaves from an untransformed potato plant, and from potato plants transformed with the p35S-Ω-ppase plasmid.

FIG. 5 shows the effect of the expression of the 35S-Ω-ppase gene in transgenic potato plants (positions 1 to 12) on the sucrose/starch ratio in the leaves of transformed plants.

C=untransformed potato plant

Figure 6:
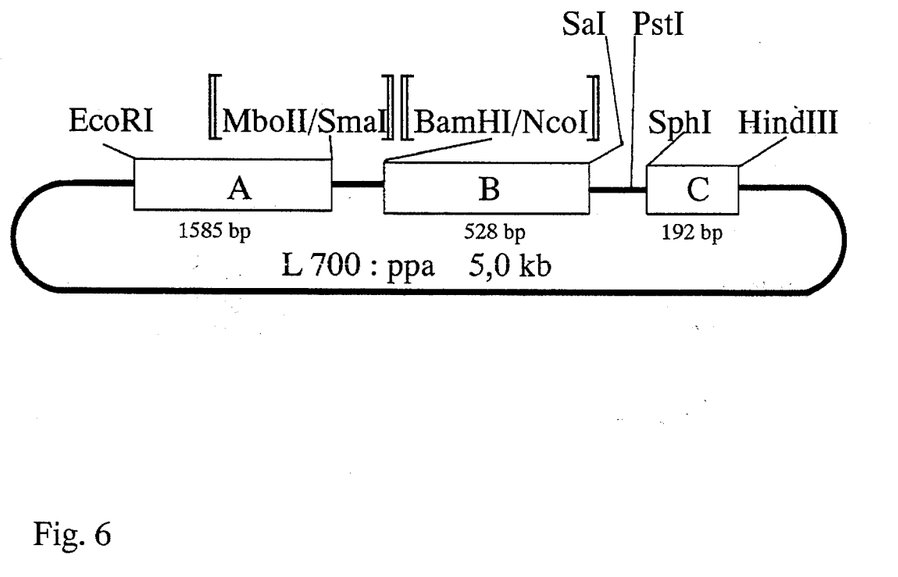
FIG. 6 shows shows the structure of the 5.0 kb plasmid L700:ppa.

FIG. 6 shows the structure of the 5.0 kb plasmid L700:ppa.

The plasmid comprises the following fragments:

A=Fragment A (1585 bp): contains the promotor of the ST-LS1 gene. That fragment includes the nucleotides, positions +1 to +1585 of the ST-LS1 gene.

B=Fragment B (528 bp): contains the protein-coding region of the inorganic pyrophosphatase (ppa). The fragment comprises the nucleotides, positions +39 to +565.

C=Fragment C (192 bp): contains the polyadenylation signal of gene 3 of the T-DNA of the Ti plasmid pTiACH5, nucleotides, positions 11749–11939.

The cleavage sites described in the Examples are also shown.

DESCRIPTION OF THE PREFERRED EMBODIMENTS

In order better to understand the Examples forming the basis of this invention, all the processes that are necessary for these tests and which are known per se will first of all be listed:

1. Cloning Process

The vector pUC18 (Yanisch-Perron et al., Gene (1985), 33, 103–119) was used for cloning.

For plant transformation, the gene constructions were cloned into the binary vector BIN19 (Bevan, Nucl. Acids Res. (1984), 12, 8711–8720).

2. Bacterial Strains

The *E. coli* strains BMH71-18 (Messing et. al., Proc. Natl. Acad. Sci. USA (1977), 24, 6342–6346) or TB1 were used for the pUC vectors. TB1 is a recombination-negative, tetracycline-resistant derivative of strain JM101 (Yanisch-Perron et al., Gene (1985), 33, 103–119). The genotype of the TB1 strain is (Bart Barrel, pers. communication): F (traD36, proAB, lacI, lacZΔM15), Δ(lac, pro), SupE, thiS, recA, Sr1::Tn10(Tc$^R$).

The plant transformation was carried out by means of the *Agrobacterium tumefaciens* strain LBA4404 (Bevan, M., Nucl. Acids Res. 12, 8711–8721, (1984); BIN19 derivative).

3. Transformation of *Agrobacterium tumefaciens*

In the case of BIN19 derivatives, the insertion of the DNA into the agrobacteria was effected by direct transformation in accordance with the method developed by Holsters et al., (Mol. Gen. Genet. (1978), 163, 181–187). The plasmid DNA of transformed agrobacteria was isolated in accordance with the method developed by Birnboim and Doly (Nucl. Acids Res. (1979), 7, 1513–1523) and was separated by gel electrophoresis after suitable restriction cleavage.

4. Plant Transformation

A) Tobacco 10 ml of an overnight culture of *Agrobacterium tumefaciens*, grown under selection, were centrifuged off, the supernatant was discarded, and the bacteria were resuspended in the same volume of antibiotic-free medium. In a sterile Petri dish, leaf discs of sterile plants (approximately 1 cm$^2$), the central vein of which had been removed, were immersed in that bacterial suspension. The leaf discs were then placed in a closely packed arrangement in Petri dishes containing MS medium (according to Murashige and Skoog, Physiologia Plantarum (1962), 15, 473–497) with 2% sucrose and 0.8% Bacto agar. After two days' incubation in the dark at 25° C., they were transferred onto MS medium containing 100 mg/l of kanamycin, 500 mg/l of claforan, 1 mg/l of benzylaminopurine (BAP), 0.2 mg/l of naphthylacetic acid (NAA) and 0.8% Bacto agar. Growing shoots were transferred onto hormone-free MS medium with 250 mg/l of claforan.

B) Potato 10 small leaves, damaged with a scalpel, of a sterile potato culture were placed in 10 ml of MS medium with 2% sucrose containing from 30 to 50 µl of an *Agrobacterium tumefaciens* overnight culture grown under selection. After from 3 to 5 minutes' gentle shaking, the Petri dishes were incubated in the dark at 25° C. After 2 days, the leaves were laid out on MS medium with 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% Bacto agar. After incubation for one week at 25° C. and 3000 lux, the claforan concentration in the medium was reduced by half. Further cultivation was effected in the manner described by Rocha-Sosa et al. in EMBO Journal 8, 29 (1989).

5. Analysis of Genomic DNA from Transgenic Plants

The isolation of genomic plant DNA was effected in accordance with Rogers and Bendich (Plant Mol. Biol. (1985), 5, 69–76.

For the DNA analysis, after suitable restriction cleavage, from 10 to 20 µg of DNA were analysed by means of Southern blotting for the integration of the DNA sequences to be investigated.

6. Analysis of the Total RNA from Transgenic Plants

The isolation of plant total RNA was carried out in accordance with Logemann et al. (Analytical Biochem. (1987), 163, 16–20).

For the analysis, 50 µg portions of total RNA were investigated by means of Northern blotting for the presence of the transcripts sought.

7. Protein Extraction

For the extraction of total protein from plant tissue, pieces of tissue were homogenised in protein extraction buffer (25 mM sodium phosphate pH 7.0, 2 mM sodium hydrogen sulphite, 2 mM phenylmethylsulphonyl fluoride (PMSF)), with the addition of 0.1% (w/v) of insoluble polyvinylpyrrolidone (PVP).

After filtering through cellulose, cell detritus was centrifuged off for 20 minutes at 10,000 revolutions per minute and the protein concentration of the supernatant was determined in accordance with the method developed by Bradford (Anal. Biochem. (1976)/72, 248–254).

8. Detection of the Inorganic Pyrophosphatase Activity (Modified According to Baykov et al., Analytical Biochemistry 171, 271–276 (1988))

The total protein was extracted from plants as described under point 7, and unmodified SB buffer (125 mM tris/HCl pH 6.8, 10% 2-mercaptoethanol, 20% glycol, 0.004% bromophenol blue) was added and the whole was added to 10% SDS polyacrylamide gels. The mixtures were denatured, not by heating, before separation in the SDS polyacrylamide gels. After electrophoretic separation, the gels were rinsed briefly in water and incubated for 1 hour at 37° C. in pyrophosphate buffer (0.05M tris/HCl pH 9.0; 0.03 mM inorganic pyrophosphate ($Na_4P_2O_7$), 5 mM $MgCl_2$). 17% by volume staining powder (140 mg of ammonium molybdate, 11.5 mg of malachite green in 10 ml of 2.5M $H_2SO_4$) was then added to the solution. The formation of a turquoise precipitate indicated pyrophosphatase activity.

9. Determination of Sucrose, Glucose, Fructose and Starch a) Extraction

Small leaf discs (diameter 10 mm) frozen in liquid nitrogen were extracted for 30 minutes at 80° C. in 0.5 ml of buffer (80% (v/v) ethanol; 10 mM HEPES pH 7.5) in a water bath. The supernatant containing the soluble components was poured off and the volume was determined. The supernatant was used to determine the soluble sugars.

The insoluble material that remained was rinsed with water and finely ground in a mortar. The extract was then boiled for 1 hour at 95° C. in 0.2M potassium hydroxide solution, neutralised with 70 µl of 1N acetic acid and then centrifuged. Aliquots of the resulting starch solution were used to determine the starch.

b) Quantitative Determination of Soluble Glucose, Fructose and Sucrose

The quantitative determination of soluble glucose, fructose and sucrose was carried out in the following test mixture:

100.0 mM imidazole-HCl, pH 6.9

1.5 mM $MgCl_2$ 0.5 mM $NADP^+$ 1.3 mM ATP

10–50.0 µl sample 1.0 U glucose-6-phosphate-dehydrogenase from yeast

The mixture was incubated for five minutes. The determination of the sugars was then carried out photometrically by the successive addition of 1.0 U hexokinase from yeast (for the determination of glucose)

1.0 U phosphoroglucose isomerase from yeast (for the determination of fructose)

20.0 U invertase from yeast (for the determination of sucrose).

c) Starch Determination

Hydrolytic enzymes were added at 55° C. to the starch solution obtained after the ethanolic extraction under a) and the whole was incubated for twelve hours in the following mixture:

50.0 mM sodium acetate, pH 4.8

1.4 U amyloglucosidase from *Aspergillus niger*

2.0 U α-amylase from porcine pancreas

After incubation, the insoluble constituents were removed by 4 minutes' centrifugation at 16,000 g. In the supernatant, the resulting glucose was then determined enzymatically, as described under b).

EXAMPLE 1

Preparation of Plasmid p35S-Ω-ppase and Insertion of the Plasmid into the Plant Genome A DNA sequence from *E. coli* K12 that codes for inorganic pyrophosphatase was provided with a promoter of the 35S RNA of cauliflower mosaic virus (CaMV) that brings about constitutive expression, a DNA segment from tobacco mosaic virus that serves as a translation amplifier, and a plant termination signal. The plant termination signal comprises the 3'-end of the poly-A side of the octopine synthase gene. The vicinity of the translation initiation codon ATG of the sequence for inorganic pyrophosphatase was subjected to a controlled mutagenesis in order to achieve optimum expression in eukaryotic cells. Plasmid p35S-Ω-ppase comprises the four fragments A, B, C and D which were cloned into the cleavage sites of the polylinker of pUC 18 (FIG. 1).

Fragment A (529 bp) contains the 35S promoter of cauliflower mosaic virus (CaMV). That fragment includes the nucleotides 6909 to 7437 of CaMV (Franck et al., Cell 21, 285–294). It was isolated in the form of Eco RI-Kpn I fragment from plasmid pDH51 (Pietrzak et al., Nucleic Acids Research 14, 5857–5868) and cloned between the Eco RI-Kpn I cleavage sites of the polylinker of plasmid pUC 18.

Fragment B contains a segment consisting of 61 nucleotides having the sequence SEQ ID NO:2

TTTACAACAATTACCAACAACAACAAA-
CAACAAACAACATTACAATTACTATTTA-
CAATTA which is homologous to a portion of the DNA segment, serving as a translation amplifier, from the tobacco mosaic virus strain U (Gallie et al., Nucleic Acids Res. 15, 3257–3273). That segment, which was produced by DNA synthesis, was provided at the 5'-end with an Asp 718 linker having the sequence

GGTACC and at the 3'-end with an Nco I-linker having the sequence

CCATGG.

Fragment B was cloned between the Kpn I and Sma I cleavage site of the polylinker of pUC 18.

Fragment C includes the protein-coding region of inorganic pyrophosphatase (ppa) from $E.$ $coli$ which comprises the nucleotides, positions +39 to +565, of the sequence according to Lahti et al., (J. Bacteriology 170, 5901–5907).

Fragment C was cloned between the Nco I site of fragment B and the Sal I site of the polylinker of pUC 18.

Fragment D (192 bp) contains the polyadenylation signal of gene 3 of the T-DNA of the Ti plasmid pTiACH5 (Gielen et al., EMBO J. 3, 835–846), nucleotides 11749–11939, which was isolated in the form of Pvu II-Hind III fragment from plasmid pAGV 40 (Herrera-Estrella et al., (1983) Nature 303, 209–213) and, after the addition of Sph I linkers to the Pvu II cleavage site, was cloned between the Sph I-Hind III cleavage sites of the polylinker of pUC 18.

The size of plasmid p35S-Ω-ppase is 4.0 kb.

Plasmid p35S-Ω-ppase was inserted into binary vectors and then inserted into tobacco and potato plants by means of the agrobacteria system. Intact and fertile plants were regenerated from transformed cells.

Analysis of the transformed plants by Southern blot analysis indicated the presence of the intact chimaeric pyrophosphatase gene in the transgenic plants.

In order to detect the RNA coded for by the pyrophosphatase gene in transgenic potato and tobacco plants, 30 μg of total RNA were isolated from the leaves of the transformed and regenerated potato and tobacco plants and from untransformed potato and tobacco plants. The RNA was investigated by means of Northern blot analysis. The analysis of the regenerated plants (potato: positions 1, 2, 8, 11, 12, 15 and 13: and tobacco: positions 21 to 26) indicated, in the tissues, RNA that hybridises specifically with the coding sequence of inorganic pyrophosphatase and that is absent in untransformed plants (potato plant, position A, tobacco plant, position B) (FIG. 2).

The detection of the new pyrophosphatase activity in protein extracts from leaves of the transgenic potato and tobacco plants transformed with the p35S-Ω-ppase plasmid was carried out in partially denatured gels, as described under point 8.

The protein extracts of transformed plants that comprise an RNA hybridising specifically with the coding sequence of inorganic pyrophosphatase exhibited an inorganic pyrophosphatase activity (potato plants: positions 1 to 7 and tobacco plants: positions 8 and 9) which was not present in untransformed plants, positions A to C (see FIG. 3).

Transgenic tobacco and potato plants were thus produced that comprise a new inorganic pyrophosphatase activity that originates from the $E.$ $coli$ gene inserted into those plants (see FIG. 3).

The regenerated tobacco and potato plants exhibited a number of differences in respect of phenotypic and biochemical parameters.

a) Transgenic Tobacco Plants

Transgenic tobacco plants having a high level of expression of the pyrophosphatase gene exhibited a marked reduction in plant size, while tobacco plants having a medium level of expression of the pyrophosphatase gene exhibited only a slight reduction in size. The compactness is not attributable to a reduction in the number of leaves but to a reduction in the internodal distance.

The young leaves of the tobacco plants that express pyrophosphatase did not exhibit any marked phenotypic differences in comparison with untransformed control plants. The older leaves of the pyrophosphatase-expressing leaves, on the other hand, exhibited a marked thickening of the leaf. In plants that express the pyrophosphatase gene to a very high degree, a bleaching of the older leaves was observed. Apart from those phenotypic differences, the tobacco plants that express the pyrophosphatase gene exhibited a marked change in the composition of the carbohydrates in leaves of different age (see FIGS. 4A, 4B, 4C, and 4D). For example, the amounts of soluble sugars, especially glucose, fructose and sucrose, were distinctly increased in all leaves compared with leaves of untransformed plants, an increase by a factor of up to 20–50 being observed in the older leaves. At the same time, at least in the older leaves, there was an increase in the amount of starch formed, but that increase was not as great as the increase in the proportion of soluble sugars, so that, overall, on the one hand a marked increase was observed in the total content of starch and soluble sugars as a result of the expression of pyrophosphatase and, on the other hand, there was a clear shift in the distribution of the photoassimilates between starch and soluble sugars towards soluble sugars.

b) Transgenic Potato Plants

Transgenic potato plants expressing the pyrophosphatase gene exhibited as the first substantial phenotypic modification a markedly compact size. The compactness is accompanied by increased branching of the plants owing to the increased formation of axial shoots. It is obvious that this compact growth has many advantages with regard to stability and sensitivity to wind.

The potato plants that express the pyrophosphatase gene also exhibited drastic changes in respect of the composition of the carbohydrates in the leaf (see FIG. 5). For example, the potato plants have an increased sucrose:starch ratio. The increase in that ratio can be as much as a factor of 20. Unlike the tobacco plants, the transgenic potato plants did not exhibit a drastic increase in hexoses (glucose and fructose).

As a result of the expression of the gene coding for inorganic pyrophosphatase in transgenic potato plants, it was possible to achieve a modification in the sucrose/starch ratio and accordingly to modify the capacity of the source leaf.

The pyrophosphatase gene can be cloned from many other sources and be used for similar experiments. In addition the primary sequence of the pyrophosphatase can be modified to achieve a higher expression level and/or to target the ppase into e.g. other subcellular organelles (chloroplasts, mitochondria, vacuole, extracellular space) or to use other promtors ensuring the expression specifically only in e.g. photosynthetically active cells, in seeds, tubers, tap roots, fruits, roots, stem, flowers etc. or under specific environmental conditions such as drought, heat, cold, high-salt soils etc.

EXAMPLE 2

Preparation of Plasmid L700:ppa and Insertion of the Plasmid into the Plant Genome A DNA sequence from *E. coli* K12 that codes for inorganic pyrophosphatase was provided with a promotor of the ST-LS1 gene (Stockhaus et al., EMBO J. 8, 2445–2451 (1989)) that brings about specific expression in photosynthetically active cells, and a plant termination signal. The plant termination signal comprises the 3'-end of the poly-A side of the octopine synthase gene. Plasmid L700:ppa comprises the three fragments A, B and C which were cloned into the cleavage sites of the polylinker of pUC 18 (FIG. 6).

Fragment A (1585 bp) contains the promotor of the ST-LS1 gene (op.cit.). That fragment includes the nucleotides +1 to +1585 of the ST-LS1 gene (Eckes et al., Mol. Gen. Genetics 205, 14–22). It was isolated in the form of a EcoRI-MboII fragment and cloned between the EcoRI-SmaI cleavage sites of the polylinker of plasmid pUC 18 after the MboII site had been flushed by T4-DNA Polymerase.

Fragment B includes the protein-coding region of inorganic pyrophosphatase (ppa) from *E. coli* which comprises the nucleotides, positions +39 to +565, of the sequence according to Lahti et al., (J. Bacteriology 170, 5901–5907). It was isolated in the form of a NcoI-SalI fragment from the plasmid p35S-Ω-ppase (cf. FIG. 1). Fragment B was cloned between the BamHI site and the SALI site of the polylinker of pUC 18 after the NcoI site and the BamHI site had been made blunt end by fill-in reactions.

Fragment C (192 bp) contains the polyadenylation signal of gene 3 of the T-DNA of the Ti plasmid pTiACH5 (Gielen et al., EMBO J. 3, 835–846) nucleotides 11749–11939, which was isolated in the form of a PvuII-HindIII fragment from plasmid pAGV 40 (Herrera-Estrella et al., (1983) Nature 303, 209–213) and, after the addition of SphI linkers to the PvuII cleavage site, was cloned between the SphI-HindIII cleavage sites of the polylinker of pUC 18.

The size of plasmid L700:ppa is 5.0 kb.

Plasmid L700:ppa was inserted into binary vectors and then inserted into tobacco and potato plants by means of the agrobacteria system. Intact and fertile plants were regenerated from transformed cells.

Analysis of the transformed plants by Southern blot, RNA blot and zymogram analysis indicated the presence and expression of the pyrophosphatase gene in the transgenic plants only in leaf tissue respectively photosynthetically active cells.

The specific expression of the *E. coli* pyrophosphatase in photosynthetically active cells (leaf) leads to an increased supply of sink organs (roots, tubers) with sucrose and thus increases yield.

---

We claim:

1. A plasmid comprising the following DNA-sequences:
   a) a promoter active in plant cells;
   b) at least one DNA sequence coding for an *E. coli* inorganic pyrophosphatase which is linked in a sense-orientation to the 3'-end of said transcriptional promoter; and
   c) a transcriptional termination sequence, wherein when said plasmid is transferred into a plant cell thereby producing a transformed cell, said transformed plant cell expresses an additional pyrophosphatase activity in the cytosol of said transformed cell, resulting in a reduction of the concentration of free pyrophosphate and an increase in the concentration of at least one of the soluble sugars of the group consisting of UDP-glucose, glucose, fructose and sucrose in said transformed plant cell compared to an untransformed plant cell.

2. A plasmid according to claim 1, wherein said transcriptional promoter is selected from the group consisting of:
   the promoter of the 35S RNA gene of the cauliflower mosaic virus and
   the promoter of the ST-LS1 gene.

3. Plasmid p 35-Ω-ppase (DSM 6141).

4. Plasmid L 700:ppa (DSM 6733

5. A method for the production of transgenic Solanaceae plants agriculturally useful for the production of soluble sugars by:
   a) transforming at least one cell from a Solanaceae plant agriculturally useful for the production of soluble sugars with a plasmid as claimed in claim 1 or 2, thereby producing at least one transformed cell, wherein said transformed cell expresses an additional inorganic pyrophosphatase activity in the cytosol of said transformed cell, resulting in a reduction of free pyrophosphate and an increase of the concentration of at least one of the soluble sugars of the group consisting of UDP-glucose, glucose, fructose and sucrose, compared to an untransformed plant cell, and
   b) using said transformed cell to produce at least one transgenic, Solanaceae plant agriculturally useful for the production of soluble sugars.

6. A method for the production of transgenic potato plants by:
   a) transforming at least one potato plant cell with a plasmid as claimed in claim 1 or 2 for the production of at least one transformed cell, wherein said DNA molecule leads upon stable integration into the plant genome to an expression of an additional inorganic pyrophosphatase activity in the cytosol of said transformed cell, which results in a reduction of the concentration of free pyrophosphate and an increase of the concentration of at least one of the soluble sugars of the group consisting of UDP-glucose, glucose, fructose and sucrose, compared to an untransformed plant cell, and
   b) using said transformed cell to produce at least one transgenic potato plant.

7. A method for the production of transgenic potato plants according to claim 6, wherein said DNA molecule comprises plasmid p 35-Ω-ppase (DSM 6141).

8. A method for the production of transgenic Solanaceae plants agriculturally useful for the production of soluble sugars according to claim 5, wherein said DNA molecule comprises plasmid p 35-Ω-ppase (DSM 6141).

9. A method for the production of transgenic potato plants according to claim 6, wherein said DNA molecule comprises plasmid L 700:ppa (DSM 6733).

10. A method for the production of transgenic Solanaceae plants agriculturally useful for the production of soluble sugars according to claim 5, wherein said DNA molecule comprises plasmid L 700:ppa (DSM 6733).

11. A method for the production of transgenic tobacco plants by:
    a) transforming at least one tobacco plant cell with a plasmid as claimed in claim 1 or 2 for the production of at least one transformed cell, wherein said DNA molecule leads upon stable integration into the plant genome to an expression of an additional inorganic pyrophosphatase activity in the cytosol of said transformed cell, which results in a reduction of the concentration of free pyrophosphate and an increase of the concentration of at least one of the soluble sugars of the group consisting of UDP-glucose, glucose, fructose and sucrose, compared to an untransformed plant cell, and
    b) using said transformed cell to produce at least one transgenic tobacco plant.

12. A method for the production of transgenic tobacco plants according to claim 11, wherein said DNA molecule comprises plasmid p 35-Ω-ppase (DSM 6141).

13. A method for the production of transgenic tobacco plants according to claim 11, wherein said DNA molecule comprises plasmid L 700:ppa (DSM 6733).

\* \* \* \* \*